US006607739B1

(12) United States Patent
Wallo

(10) Patent No.: US 6,607,739 B1
(45) Date of Patent: Aug. 19, 2003

(54) DISPENSING ARTICLE

(75) Inventor: Warren Wallo, Belle Mead, NJ (US)

(73) Assignee: Johnson & Johnson Consumer Companies, Inc., Skillman, NJ (US)

(*) Notice: Subject to any disclaimer, the term of this patent is extended or adjusted under 35 U.S.C. 154(b) by 0 days.

(21) Appl. No.: 09/503,261

(22) Filed: Feb. 14, 2000

(51) Int. Cl.$^7$ ............................ A61F 9/00; A01N 25/34

(52) U.S. Cl. ........................ 424/404; 424/401; 424/402

(58) Field of Search ................................ 424/401, 402, 424/404; 510/108, 119, 130, 140

(56) References Cited

U.S. PATENT DOCUMENTS

| | | | | | |
|---|---|---|---|---|---|
| 2,102,858 | A | * | 12/1937 | Schlumbohm | 206/46 |
| 2,209,914 | A | | 7/1940 | Gerber et al. | 128/272 |
| 2,961,677 | A | | 11/1960 | Zecchini | 15/131 |
| 2,980,941 | A | | 4/1961 | Miller | 15/506 |
| 3,054,148 | A | | 9/1962 | Zimmerli | |
| 3,306,292 | A | * | 2/1967 | Spees | 128/268 |
| 3,324,500 | A | | 6/1967 | Fuller et al. | 15/539 |
| 3,334,374 | A | | 8/1967 | Watkins, Jr. | 15/539 |
| 3,334,790 | A | | 8/1967 | Eaton | 222/107 |
| 3,362,776 | A | | 1/1968 | Knorr | 401/8 |
| 3,394,211 | A | | 7/1968 | MacDuff | |
| 3,466,131 | A | | 9/1969 | Arcudi | 401/132 |
| 3,635,567 | A | * | 1/1972 | Richardson, Jr. | 401/132 |
| 3,768,916 | A | | 10/1973 | Avery | 401/132 |
| 3,776,644 | A | | 12/1973 | Baker | 401/7 |
| 3,826,259 | A | | 7/1974 | Bailey | 128/269 |
| 3,929,135 | A | | 12/1975 | Thompson | |
| 4,173,978 | A | | 11/1979 | Brown | 128/269 |
| 4,183,684 | A | | 1/1980 | Avery, Jr. | 401/133 |
| 4,469,463 | A | | 9/1984 | Van Overloop | 401/134 |
| 4,478,530 | A | | 10/1984 | Van Overloop | 401/134 |
| 4,515,703 | A | * | 5/1985 | Haq | 252/92 |
| 4,525,091 | A | | 6/1985 | Van Overloop | 401/134 |
| 4,563,103 | A | | 1/1986 | Van Overloop et al. | 401/134 |
| 4,576,737 | A | | 3/1986 | Johnson | |
| 4,596,481 | A | | 6/1986 | Tanaka | |
| 4,741,877 | A | | 5/1988 | Mullane, Jr. | |
| 4,812,067 | A | | 3/1989 | Brown et al. | 401/132 |
| 4,904,524 | A | | 2/1990 | Yoh | 428/311.3 |
| 5,090,832 | A | | 2/1992 | Rivera et al. | 401/132 |
| 5,242,433 | A | * | 9/1993 | Smith et al. | 604/289 |
| 5,254,109 | A | * | 10/1993 | Smith et al. | 604/289 |
| 5,326,685 | A | | 7/1994 | Gaglio et al. | |
| 5,380,110 | A | * | 1/1995 | Festa | 401/132 |
| 5,492,646 | A | | 2/1996 | Langley et al. | |
| 5,498,378 | A | | 3/1996 | Tsaur et al. | |
| 5,538,732 | A | | 7/1996 | Smith et al. | |
| 5,558,874 | A | | 9/1996 | Haber et al. | 424/402 |
| 5,620,694 | A | | 4/1997 | Girardot | 424/402 |
| 5,681,574 | A | | 10/1997 | Haber et al. | 424/402 |
| 5,720,966 | A | | 2/1998 | Ostendorf | 424/402 |
| 5,727,728 | A | | 3/1998 | Sainz et al. | |
| 5,744,149 | A | | 4/1998 | Girardot | 424/402 |
| 5,795,644 | A | | 8/1998 | Delarosa | |
| 5,802,655 | A | | 9/1998 | Denton | 15/104.93 |
| 5,839,842 | A | | 11/1998 | Wanat et al. | |

FOREIGN PATENT DOCUMENTS

| | | |
|---|---|---|
| EP | 0 032 793 | 7/1981 |
| EP | 0 170 010 | 8/1985 |

(List continued on next page.)

*Primary Examiner*—Thurman K. Page
*Assistant Examiner*—S. Tran
(74) *Attorney, Agent, or Firm*—Erin M. Harriman

(57) ABSTRACT

An article including a first exterior layer; a second exterior layer; and a cell layer having at least one cell containing an active material wherein at least one layer is an apertured film and the cell layer is disposed between the two exterior layers. Typically the article is useful for cleaning or treating surfaces including skin, metal, wood, glass, and plastics.

19 Claims, 3 Drawing Sheets

FOREIGN PATENT DOCUMENTS

| | | | | |
|---|---|---|---|---|
| EP | 0 170 821 | | | 8/1986 |
| EP | 0 252 459 | | | 1/1988 |
| EP | 0 388 718 | | | 9/1990 |
| EP | 0 266 929 | B1 | | 12/1992 |
| EP | 0 515 703 | A1 | | 12/1992 |
| EP | 0 653 635 | A1 | | 5/1995 |
| EP | 0 728 475 | A2 | | 8/1996 |
| EP | 0 873 711 | A2 | | 10/1998 |
| NZ | 205183 | | * | 1/1987 |
| WO | WO 89/07935 | | | 9/1989 |
| WO | WO 98/18444 | | | 5/1990 |
| WO | WO 95/00116 | | | 1/1995 |
| WO | WO 95/26670 | | | 10/1995 |
| WO | WO 96/04836 | | | 2/1996 |
| WO | WO 96/10429 | | | 4/1996 |
| WO | WO 96/11673 | | | 4/1996 |
| WO | WO 96/23439 | | | 8/1996 |
| WO | WO 97/07780 | | | 3/1997 |
| WO | WO 97/07781 | | | 3/1997 |
| WO | WO97/24053 | | | 7/1997 |
| WO | WO 97/35564 | | | 10/1997 |
| WO | WO 97/38843 | | | 10/1997 |
| WO | WO 98/18441 | | | 5/1998 |
| WO | WO 98/18442 | | | 5/1998 |
| WO | WO 98/18445 | | | 5/1998 |
| WO | WO 98/18446 | | | 5/1998 |
| WO | WO 98/28399 | | | 7/1998 |
| WO | WO 98/55109 | | | 10/1998 |
| WO | 98/50012 | | | 11/1998 |
| WO | 99/09873 | | | 3/1999 |

* cited by examiner

DISPENSING ARTICLE

BACKGROUND OF THE INVENTION

1. Field of the Invention

This invention relates to an article that is useful for cleansing or treating various surfaces. More particularly, this invention is related to an article containing a top layer, a bottom layer, and at least one cell therebetween, the latter of which contains an active material.

2. Description of the Prior Art

Many scrubbing or scouring implements or articles are designed for cleaning or treating surfaces such as skin, wood, glass, plastics, and metal. As used herein, by "treating" is meant applying a material such as a medicine, skin care product, wax, polish, and the like to a desired location. Generally, the scrubbing implements are made from materials such as sponges, woven fabrics, or nonwoven fabrics. These scrubbing implements may be supplied either with the accompanying cleaning or treating solution in a system, or alternatively may be supplied as a stand-alone item. When using such implements, a consumer disadvantageously is required to perform a three-step process: first the cleaning or treating solution is measured; second, the cleaning or treating solution is dispensed onto a scrubbing implement; and third, the scrubbing implement is then used with the cleaning or treating solution to clean or treat a surface. Not only is this process often messy, but it is also inconvenient to the user.

Several attempts have been made to make to reduce the inconveniences incurred with cleaning or treating processes. For example, U.S. Pat. No. 2,102,858 discloses an absorbent pad material that is pre-loaded with a liquid cleaning substance, then stored in a water proof wrapper. When desired, the absorbent pad is removed from the wrapper and then used for cleaning purposes. One disadvantage to this design is that the liquid cleaner is pre-loaded on the absorbent pad; therefore, the amount of liquid cleaner utilized can not be adjusted by the user. In addition, consumers are unable to easily rinse the cleansing product from the absorbent pad.

U.S. Pat. No. 3,635,567 discloses a disposable combination package and soft absorbent pad applicator. Within the applicator is a rupturable cell, which houses a liquid. Upon rupturing the cell, the liquid is released for use into the absorbent pad. Disadvantageously, the absorbent pad tends to absorb the cleaning or treating solution, and therefore precludes a thorough cleaning of the pad after use. In addition, the absorbent pad may also promote microbial growth because it tends to stay wet for a considerable period of time. Further, the design provides only one cell for housing a cleaning or treating solution, and thus has limited reusability.

U.S. Pat. No. 4,515,703 discloses a perforated article having a top substrate and a bottom substrate wherein each substrate is comprised of a paper or nonwoven having an inner liquid impermeable thermoplastic material laminated thereto. Between the substrates is an active material that is arranged into compartments via sealing the article. The size of the perforations is dependent upon the type of active material contained therein. Due to the use of paper and nonwoven exteriors, these articles disadvantageously tend to retain moisture, which promotes microbial growth. Furthermore, such exteriors do not contribute to improved foaming characteristics when foamable surfactants are selected as the active material.

It would be desirable to have a re-usable cleaning product that can be used with a variety of cleaning or treating solutions, is easily cleaned after use, and dries quickly. Moreover, when foamable surfactants are used therein, it would be further desirable to have a product having superior foaming capabilities.

SUMMARY OF THE INVENTION

In accordance with this invention, there is an article comprising:

a first exterior layer;

a second exterior layer;

and a cell layer having at least one cell containing an active material, wherein at least one of the exterior layers is an apertured film and the cell layer is disposed between the first exterior layer and the second exterior layer.

The articles of this invention are not only reusable, but also easily cleaned and dried after use. Moreover, the articles are not only versatile in view of the fact that they may be incorporated with a variety of cleaning or treating solutions, but, when used with foamable surfactants, are also capable of producing superior foam.

DESCRIPTION OF THE DRAWINGS

The invention will be more fully understood and further advantages will become apparent when reference is made to the following detailed description of the invention and the accompanying drawing in which.

DESCRIPTION OF PREFERRED EMBODIMENT

It is believed that one skilled in the art can, based upon the description herein, utilize the present invention to its fullest extent. The following specific embodiments are to be construed as merely illustrative, and not limitative of the remainder of the disclosure in any way whatsoever.

Unless defined otherwise, all technical and scientific terms used herein have the same meaning as commonly understood by one of ordinary skill in the art to which the invention belongs. Also, all publications, patent applications, patents, and other references mentioned herein are incorporated by reference.

As used herein, "width" shall mean the diameter when referring to generally circular apertures/holes or the largest distance across a given shape when referring to non-circular apertures/holes.

Figure 1:
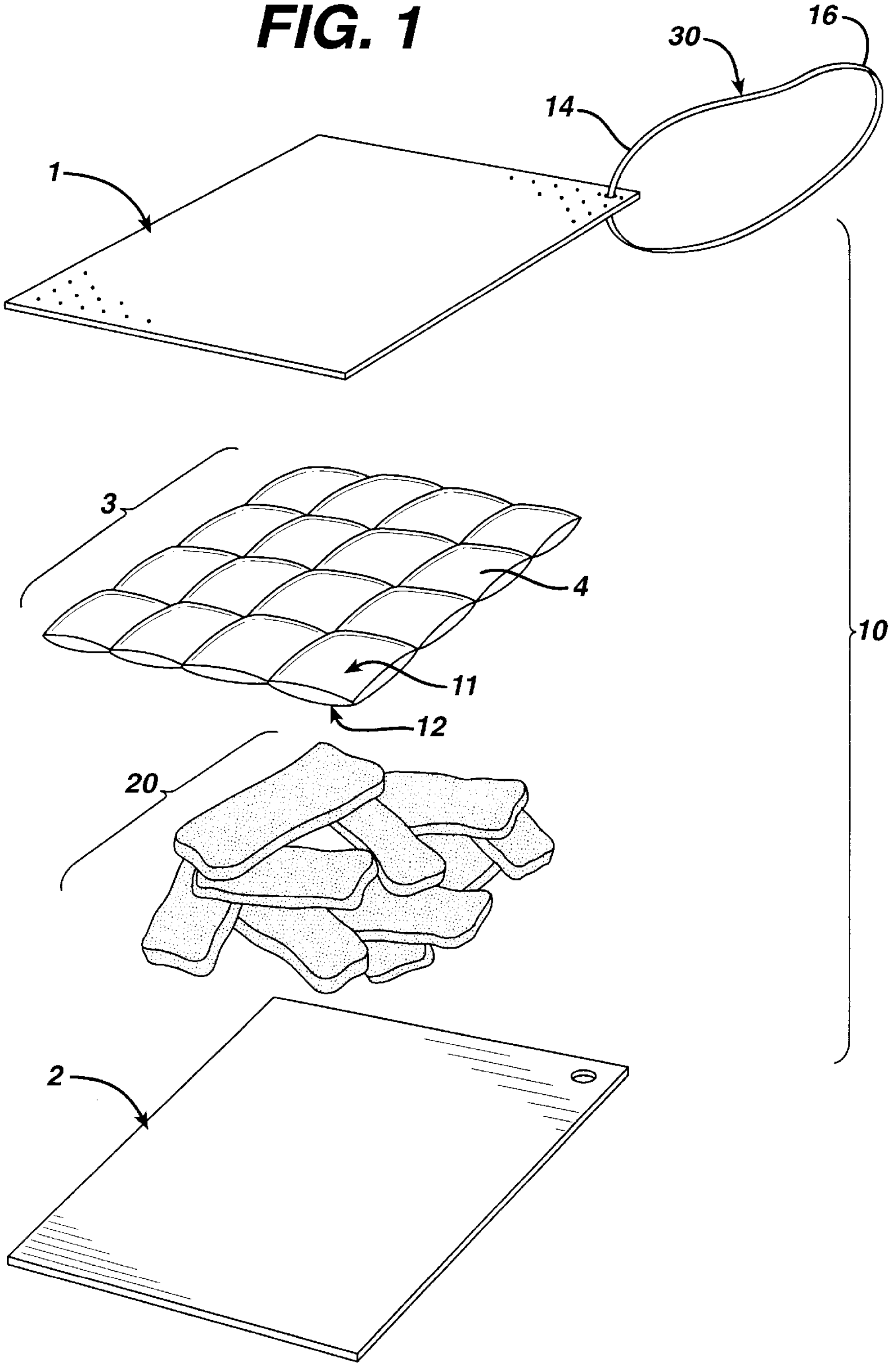
FIG. 1 is a representation of an expanded perspective view of the article of the present invention.

As shown in FIG. 1, the present invention provides a scrubbing or scouring article including: a) a first exterior layer 1; b) a second exterior layer 2; and c) a cell layer 3 comprised of at least one cell 4. The cell layer 4 is disposed between the first and second exterior layers 1, 2. The first exterior layer 1 is attachable, either removably or fixedly, to the second exterior layer 2.

The first exterior layer 1 and the second exterior layer 2 may be made of the same or different materials; however, at least one exterior layer must be comprised of an apertured or perforated film. The other exterior layer may be made from polymeric sheets that optionally may be textured, i.e. apertured films or embossed films; substantially coarse mesh, such as that used in known diamond mesh puffs; porous foams; reticulated foams; natural fibers (e.g. wood, or cotton fibers); synthetic or polymeric fibrous sheets; combinations thereof and the like, with apertured polymeric films being the material of choice. The fibrous sheets may be comprised of either woven or nonwoven fabrics. For example, the sheet may be comprised of a spunbonded or meltblown web or polyolefin fibers or may be a bonded-carded web comprised of natural and/or synthetic fibers.

Suitable polymer films nonexclusively include those comprised of polyester, polypropylene, polyethylene, ethylene vinyl acetate, metallocene polyethylene, and blends and copolymers thereof. Where ethylene vinyl acetate copolymers are utilized, a vinyl acetate content from about 9 weight percent to about 28 weight percent, based upon the total weight of the copolymer, is preferred. The polymeric fibrous sheets may also be comprised of any of these polymers. Examples of suitable commercial polymeric apertured films include those available from Tredegar Film Products, Inc. under the tradename, “VisPore®” or those from Polymer Group, Inc. under the tradename, “Reticulon®, with the “VisPore®” film being preferred.

Suitable apertured films may be prepared by a process which generates macroporous cone shaped holes or pores. The pores of the perforated films may be created in the films via known processes as described in, for example, U.S. Pat. Nos. 3,054,148; and 4,741,877; or via a post treatment perforation step, see U.S. Pat. Nos. 3,929,135 and 3,394,211 (blast of heated air creates a pressure differential across a perforated forming surface covered with a pre-formed film). Generally speaking, the resulting apertured film possesses a “rough” side, which contains the raised protuberances and an alternative “smooth” side. By “smooth” side, it is meant the side from which the raised protuberances originate. The protuberances in apertured films are generally cone-shaped. In uses of the articles of the present invention where exfoliation is of concern, it is preferable to have the protuberances facing outward.

Although the type of apertures, as well as their depth and width, in the apertured film may vary depending upon, for example, the type of active material to be used with the article, the desired rate at which active-material, e.g., soap, to be released to the surface of the article, the ease of rinsability desired, the desired end use of the article, the size of bubbles desired, and the volume of foam desired, generally the apertured film contains from about 1.6 apertures/$cm^2$ to about 248 apertures/$cm^2$, preferably from about 3 apertures/$cm^2$ to about 30 apertures/$cm^2$, and most preferably from about 5 apertures/$cm^2$ to about 15 apertures/$cm^2$. Preferably, for uses of the articles on locations such as the face, where softness is of concern, the film contains from about 80 apertures/$cm^2$ to about 200 apertures/$cm^2$. Preferably, for uses of the articles on locations such as the arms, where volume of foam is of concern, the film contains from about 5 apertures/$cm^2$ to about 15 apertures/$cm^2$.

The width of the apertures, as measured across the “smooth” side of the apertured film, ranges in size from about 1 mm to about 22 cm, and preferably from about 2 mm to about 10 mm. In embodiments where it is desirable to slowly deplete the soap from the article, it is preferable to use film with apertures having a relatively smaller width, i.e. less than about 5 mm and preferably greater than 2 mm.

The apertures may be of any shape that can perforated into the film. Although the shape of the aperture will generally depend upon, for example, aesthetics, the type of active material to be used with the article, the desired rate at which the active material, e.g., soap, to be released to the surface of the article, the ease of rinsability desired, the desired end use of the article, the size of bubbles desired, and the volume of foam desired, the shape of the aperture, as it appears on the “smooth” side of the film, is typically in the general form of circles, honeycombs, hearts, pears, squares, hexagons, triangles, pentagons, stellates, rectangles or combinations thereof, with the general circular shapes and hexagonal shapes being most preferred.

Although the post-textured basis weight of the film may vary depending upon, for example, the desired end use of the article and the desired aesthetic appearance and feel of the article, generally the apertured film has a basis weight thickness of about 10 $g/m^2$ to about 80 $g/m^2$, and preferably from about 20 $g/m^2$ to about 50 $g/m^2$.

Apertured films suitable for use in the articles of the present invention have an open area of no more than about 45%, and preferably greater than about 15% and no more than about 35%, based upon the total area (both film and void space) of the apertured film. As used herein, “open area” is a measure of the void space or area fraction measured as the sum of the exit opening areas of the protuberances on the rough side of the apertured film divided by the total area examined.

In one embodiment, the extured films suitable for use in the articles of the present invention may preferably possess general mechanical properties as shown below in Table A:

TABLE A

Mechanical Properties - Perforated Films

| Type of Material | Force to stretch to 20% elongation* N/m (lb./in) | Force to stretch to 50% elongation* N/m (lb./in) | Direction of Stretch | Tensile Strength* N/m (lb./in) | Elasticity# |
|---|---|---|---|---|---|
| Perforated Film suitable for use in present invention | 25–263 (0.2 to 1.5) and preferably 35–175 (0.2 to 1.0) | 88–250 (0.5 to 2.0) and preferably 88–263 (0.5 to 1.5) | Machine | >263 (>1.5) | About 60% - less than about 100%, and preferably from about 80% to less than about 100% |

*using ASTM D-882
#measured by the percent recovery time from a 50% elongation using an Instron testing device The orientation of the apertured films will also depend upon the intended final use of the article. For example, when the article is intended to provide exfoliating properties, the apertured film may be oriented such that the rough side, i.e. the side containing the cone protuberances, faces outward and thus contacts the skin. Alternatively, where a smooth feel to the skin is desired, the smooth side of the apertured film may face outward and thus contact the skin. The article may also be designed such that the first exterior layer contains the apertured film with the rough side facing outward, while the second exterior layer contains the apertured film with the smooth side facing outward. In addition, the article can be made from more than one type of apertured film, i.e. different aperture shapes and/or sizes, in order to provide different "skin feel" or functions on either exterior side of the article.

Optionally at least one of the exterior layers 1, 2 may contain an effective amount of additive agents such as anti-bacterial-agents, colorants, fragrances, and mixtures thereof. The additive agents may be applied to the film via a variety of known methods such as, for example, via spray coating, or may be incorporated into the film during its production. While the amount of additive agent on or in the exterior layer will depend upon, for example, the desired end use of the article, the type of additive agent selected, the shelf-life of the additive agent, typically the film will contain from about 0.01 $mg/cm^2$ to about 10 $mg/cm^2$ and preferably from about 0.1 $mg/cm^2$ to about 1.0 $mg/cm^2$ of additive agent.

Examples of a suitable anti-bacterial agent includes those triclosan containing agents available from Microban Products Company under the tradename, "Microban™."

The article 10 of the present invention is further comprised of a cell layer 3 that contains at least one cell 4, and preferably a plurality of cells disposed between the first exterior layer 1 and the second exterior layer 2. Each cell 4 is comprised of an upper cell film 11 and a lower cell film 12.

The cells may be made from any cell film that includes but is not limited to water insoluble film, oil-insoluble film, or combinations thereof, which are capable of being sealed while containing an active material enclosed therein. Although the cell film may possess small perforations, e.g. from about 0.2 mm to about 1.2 mm in width, it is preferred that the cell film does not possess perforations having a width greater than about 0.2 mm.

Suitable water insoluble films may be comprised of materials nonexclusively including polyvinyl chloride, polyvinylidine chloride, polyethylene, polypropylene, vinyl chloride copolymers, ethylene vinyl alcohol, and blends and copolymers thereof. Preferably, the water insoluble film also possesses a low moisture vapor permeability, i.e. from about 10 $g/m^2/24$ hr/day to about 500 $g/m^2/24$ hr/day, and preferably from about 50 $g/m^2/24$ hr/day to about 100 $g/m^2/24$ hr/day.

Although a variety of cell films may be used to produce the cells, it is desirable to use a cell film that possesses a sufficient strength to contain the active material therein during storage, but flexible enough for a consumer to puncture or "pop" through the cell film to enable usage of the product contained therein.

Each cell may contain an upper cell film 11 that is the same or different from the bottom cell film 12 with respect to thickness, composition, etc. The thickness of the cell film may range from about 0.5 mil to about 3 mil, and preferably about 1 mil to about 2 mil. For uses of the article 10 by persons such as children, the elderly, and those of limited strength, the use of thinner cell films, i.e. less than about 2.0 mil, may be utilized. In a preferred embodiment, the cell film is comprised of a polyvinylidene and polyvinyl chloride film available from S. C. Johnson & Son, Inc. under the tradename, "Saran Wrap."

In an alternative embodiment, the cell film may be comprised of a material that precludes the active material contained within the cell from escaping unless the article is dipped in a liquid that dissolves or disperses out the active material. Examples of such materials include water soluble materials such as water soluble films comprised of polyvinyl alcohol, cellulose derivatives such as methylcellulose, hydroxyethylcellulose, carboxymethylcellulose, gelatin, and those disclosed in Davidson, Robert L., et al., "Water Soluble Resins," Ch. 2–9 (1968), and blends and copolymers thereof. The thickness of the water insoluble film may range from 0.1 mil to about 5.0 mil, and preferably from about 0.5 mil to about 2.0 mil. The active material may be dispensed from the cell having cell film walls comprised of water soluble materials by wetting the device with a sufficient amount of water needed to solubilize the walls.

Depending upon the final use of the article, the clarity of the film used in the cells may become an important parameter for this film, and the addition of color to such film may also be useful to differentiate certain closed cells as well as the cleaning/treating solutions within the cells.

The cell layer 3 may be comprised of at least one cell, a row of cells or a multiple matrices of cells. Although the amount of cells and the shapes thereof will depend upon, for example, the desired appearance of the article 10 and the active material contained therein, the cell layer 3 preferably contains a plurality of cells.

In one embodiment, a row of multiple cells may be utilized in the article, and the cells optionally be labelled with, for example, the different days of the week; an "AM and PM;" or a sun or moon in order to specify when to apply the active material and/or the name of the active material therein.

Using offset spacing, single bursting cells could be used in series for treatments, e.g. a cell containing shampoo, adjacent to a cell containing conditioner, which is adjacent to a cell containing hair styling gel. In an alternative embodiment, a given cell may be placed directly over another cell for the safe storage of different, incompatible active materials that may be activated in one step for simultaneous use at treatment time. In this way, the article can be used for regiment therapies and multiple cleaning or treating solutions.

Although the thickness of the cell layer 3 will depend upon the type and amount of active material used, it typically may range from about 0.2 cm to about 2 cm.

At least one cell in the cell layer 3 contains an active material, which may be in the form of a liquid, a solid, a semi-solid, a sol, or a gel. The term "active material," as used herein is not intended merely to include detergent-active materials but also to include any substance capable of delivery via an article according to the present invention to give a benefit.

Examples of suitable active materials include known cleansers; i.e. surfactants and soaps; conditioners; moisturizers; bubble bath compositions; shaving foams; skin treatment agents such as sunscreens; tanning agents; anti-acne agents; anti-aging, i.e. wrinkles, fine lines, and other manifestations of photodamage, agents; anti-irritant agents; perfumes/fragrances and the like.

Examples of suitable cleansers and conditioners include those disclosed in U.S. Pat. No. 5,804,539. Cleansers having low irritation properties such as shampoos available from Johnson & Johnson Consumer Companies, Inc., under the tradename, "Johnson's Baby Shampoo," and washes available from Johnson & Johnson Consumer Companies, Inc., under the tradename, "Johnson's Baby Bath," are preferred.

Examples of suitable sunscreens include agents nonexclusively include butyl methoxydibenzoylmethane, octyl methoxycinnamate, oxybenzone, octocrylene, octyl salicylate, phenylbenzimidazole sulfonic acid, ethyl hydroxypropyl aminobenzoate, menthyl anthranilate, aminobenzoic acid, cinoxate, diethanolamine methoxycinnamate, glyceryl aminobenzoate, titanium dioxide, zinc oxide, oxybenzone, padimate o, red petrolatum, and mixtures thereof.

Examples of suitable tanning agents include dihydroxyacetone.

Examples of suitable anti-acne agents include, but are not limited to topical retinoids (tretinoin, isotretinoin, motretinide, adapalene, tazarotene, azelaic acid, retinol); salicylic acid; benzoyl peroxide; resorcinol; antibiotics such as tetracycline and isomers thereof, erythromycin, and the anti-inflammatory agents such as ibuprofen, naproxen, hetprofen; botanical extracts such as alnus, arnica, artemisia capillaris, asiasarum root, birth, calendula, chamomile, cnidium, comfrey, fennel, galla rhois, hawthrom, houttuynia, hypericum, jujube, kiwi, licorice, magnolia, olive, peppermint, philodendron, salvia, sasa albomarginata; imidazoles such as ketoconazole and elubiol, and those described in Gollnick, H et al. 196(I) Dermatology Sebaceous Glands, Acne and Related Disorders, 119–157 (1998), which is incorporated by reference herein, and mixtures thereof.

Preferred anti-acne agents include benzoyl peroxide, retinol, elubiol, antibiotics, and salicylic acid, with retinol and tretinoin being most preferred.

Examples of suitable anti-aging, i.e. wrinkles, fine lines, and other manifestations of photodamage, comprising topically applying the above-described delivery system composition, the relevant benefit agent, and the optional detergent to the skin of an animal or human at a desired area, wherein the benefit agent is comprised of an effective amount of an anti-acne agent or an anti-aging agent, respectively.

Examples of suitable anti-aging agents include, but are not limited to inorganic sunscreens such as titanium dioxide and zinc oxide; organic sunscreens such as octyl-methyl cinnamates and derivatives thereof; retinoids; vitamins such as vitamin E, vitamin A, vitamin C, vitamin B, and derivatives thereof such as vitamin E acetate, vitamin C palmitate, and the like; antioxidants including beta carotene, alpha hydroxy acid such as glycolic acid, citric acid, lactic acid, malic acid, mandelic acid, ascorbic acid, alpha-hydroxybutyric acid, alpha-hydroxyisobutyric acid, alpha-hydroxyisocaproic acid, atrrolactic acid, alpha-hydroxyisovaleric acid, ethyl pyruvate, galacturonic acid, glucopehtonic acid, glucopheptono 1,4-lactone, gluconic acid, gluconolactone, glucuronic acid, glucurronolactone, glycolic acid, isopropyl pyruvate, methyl pyruvate, mucic acid, pyruvia acid, saccharic acid, saccaric acid 1,4-lactone, tartaric acid, and tartronic acid; beta hydroxy acids such as beta-hydroxybutyric acid, beta-phenyl-lactic acid, beta-phenylpyruvic acid; botanical extracts such as green tea, soy, milk thistle, algae, aloe, angelica, bitter orange, coffee, goldthread, grapefruit, hoellen, honeysuckle, Job's tears, lithospermum, mulberry, peony, puerarua, nice, safflower, and mixtures thereof.

Preferred anti-aging agents include retinoids, antioxidants, alpha-hydroxy acids and beta-hydroxy acid with retinol and tretinoin being most preferred.

Examples of suitable anti-irritant agents include colloidal oatmeal, oat extract, agents known for reducing the symptoms of diaper rash such as dimethicone, zinc oxide and combinations thereof and the like.

Water or other suitable solvents may be contained in cells to enable use of an article without a sink or other source of water.

In a preferred embodiment, the article contains a plurality of cells having upper and lower cell films 11, 12 comprised of polyvinylidene and polyvinyl chloride and about 1 mL of a cleansing wash available from Johnson & Johnson Consumer Companies, Inc. under the tradename, "Purpose Gentle Cleansing Wash," in each cell. The cells are arranged in about a 5×7 matrix measuring about 7.5 cm wide by about 9 cm long by about 0.35 cm thick.

Different active materials can be included in the same or separate cells within a given article depending upon the type and amount of active material and the desired final use of the article. Suitable amounts of cleaning or treating solutions will vary depending upon the active material utilized, but generally may range from 0.1 mL to 50 mL, and preferably from 1 mL to 10 mL.

Each cell may be prepared individually by securing the periphery of the cell together via means known in the art, e.g., heat sealing, after the cell is loaded with the desired amount of active material. Alternatively, one sheet of cell film may be folded upon itself or two independent cell films may be disposed on top of another, then each cell may be formed by heat sealing the cell film combination in accordance with the desired cell shape. In one preferred embodiment, a multiplicity of cells may be supplied in a sheet having separate columns of cells. Each column may then be filled with the desired active material. See also U.S. Pat. No. 4,515,703.

Optionally, the article 10 may further comprise a core layer 20 disposed between the upper exterior layer 1 and the lower exterior layer 2. The core layer may be comprised of any material capable of providing the article 10 with softness, greater overall structural thickness, and/or improved lather and is preferably hydrophobic. Examples of suitable materials include, but are not limited to nonwovens; wovens; sponges; open-celled foam of a natural or synthetic source; extruded plastic scrim such as loofah, or netting; apertured films, embossed films, and combinations thereof. Particular examples of such materials include those set forth above with respect to the exterior layers. A preferred embodiment utilizes a core layer comprised of a diamond mesh used in body poufs available from San Francisco Soap Company, which has been cut into strips about 10 cm wide by 15 cm long, and/or an apertured film available from Tredegar Film Products, Inc. under the tradename, "Vispore™ 16013," which has been cut into strips about 1.25 cm wide by 8 cm long; however, the size of these strips is not critical.

Although the thickness of the core layer 20 may depend upon the type of core layer selected, and the desired end use of the article, typically the core layer has a thickness of from about 0 cm to about 5 cm, and preferably from about 1 cm to about 3 cm.

Figure 2A:
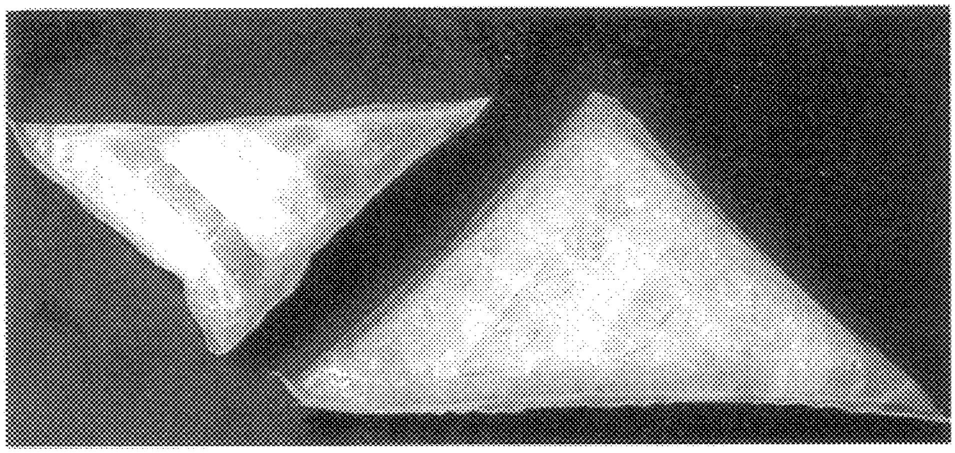
FIG. 2A is a representation of the top view of a triangular-shaped article of the present invention.
Figure 2B:
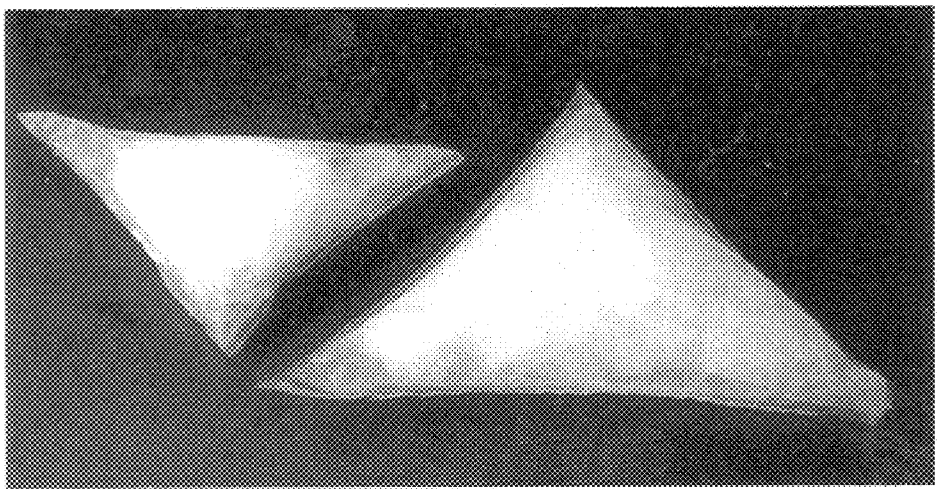
FIG. 2B is a representation of the bottom view of the article of FIG. 2A.
Figure 3A:
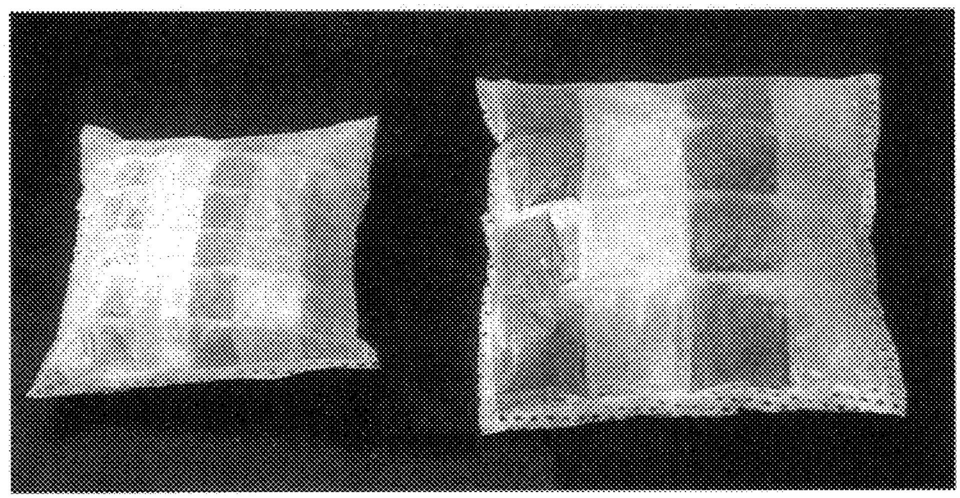
FIG. 3A is a representation of the top view of a rectangular-shaped article of the present invention.
Figure 3B:
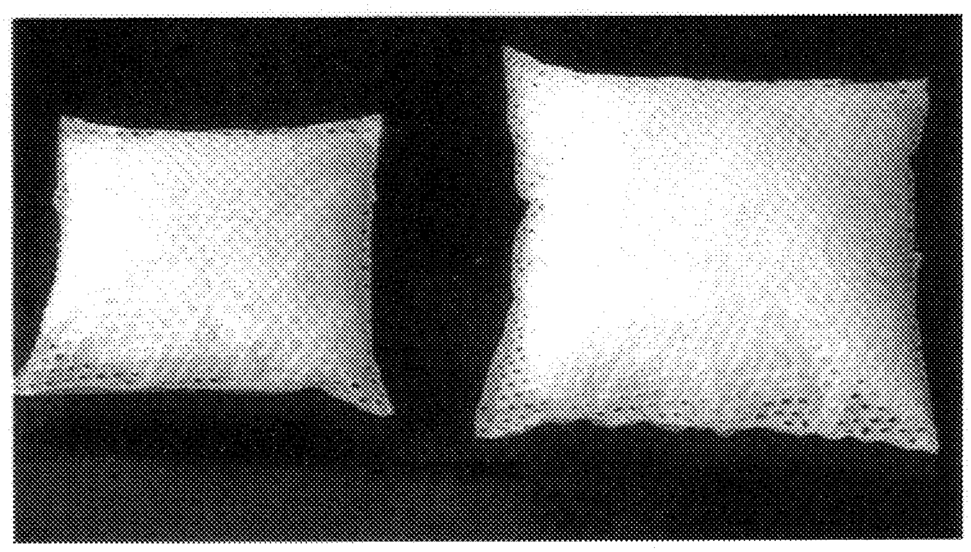
FIG. 3B is a representation of the bottom view of the article of FIG. 3A.

Although the shape and size, i.e. length, width, and thickness, of the overall article 10 will depend upon the desired use of the article and the components selected for use in the article, typically the article has a length of from about 4 cm to about 20 cm, and preferably from about 5 cm to about 15 cm, a width of from about 3 cm to about 15 cm, and preferably from about 4 cm to about 10 cm, and a depth of from about 1 cm to about 8 cm, and preferably from about 3 cm to about 6 cm. The overall shape of the article is not critical as shown in FIGS. 2A and B, which illustrate a triangular article, and FIGS. 3A and B, which illustrate a rectangular article.

Optionally, other materials can be disposed within the article 10 to impart additional sensory experiences, for example "popping" sounds. In one embodiment, polymeric film cells filled with a gas, e.g. commercially available "bubble-wrap" material, may be placed inside the article in locations that correspond to the filled cells. In this embodiment, the user experiences a sound from the breaking of both the cell film containing the active material, as well as the cell of the corresponding "bubble-wrap."

The overall article 10 may be formed by any means for attaching the upper exterior layer 1 to the lower exterior layer 2, either directly or indirectly, with the cell layer 3 therebetween. More specifically, the article of the present invention may be made by removably attaching, or preferably substantially permanently attaching, the first and second exterior layers 1, 2 by any attaching means known in the art. As used herein, "substantially permanently" means a period of time at least as long as the article is suitable for scrubbing or scouring uses. Alternatively, the first exterior layer 1 may be removably or substantially permanently attached to the cell layer 3, which is then removably or substantially permanently attached to the second exterior layer 2.

Examples of suitable attaching methods include snaps, heat sealing with a sealer capable of reaching a temperature greater than the melting temperature of the film; ultrasonic sealing; pressure sealing; tying with a ribbon, cord, strip, string, band, and the like; applying hooks and loops such as that registered as "VELCRO", hot or cold adhesive, elastic, tape such as double-sided adhesive tape, heat shrinkable film, or other known fastening article thereto; and the like, and combinations thereof. See U.S. Pat. No. 4,515,703. Preferably the attaching means is comprised of heat sealing the periphery of the article.

In one embodiment, the upper exterior layer 1 may be partially attached to the lower exterior layer 2 to form a pocket, the cell layer 3 is inserted into the pocket, and then the upper and lower exterior layers are attaching along the open end of the pocket. Alternatively, the cell layer 3 may be disposed between such exterior layers 1, 2 prior to performing the attachment. In embodiments wherein it is desirable to insert new cell layers when the existing cell layers have been expended, it is preferable to use a removably attachable attaching method along at least one side of the article.

The cell layer 3 may contain cells that are pre-filled, or the cells may be filled while disposed between the exterior layers. The core layer 20 may be inserted between the exterior layers 1, 2 either before or after the addition of the cell layer 3 thereto.

Optionally, the article 10 may further comprise a holding means 14 to enable the user to hold the article during use. In addition, this holding means 30 may also be used to hang the article for storage and drying after use. Examples of suitable holding articles nonexclusively include those disclosed in U.S. Pat. No. : 5,727,278, as well as straps, handles, knobs, hooks, with looped straps being preferred. In an alternative embodiment, the holding means may be a character figure, such as a character's head. Suitable materials for the holding articles nonexclusively include hooks and loops such as that registered as "VELCRO", magnets, plastics, rubbers, and synthetic elastics, and combinations thereof. The location of the holding means is not critical.

In embodiments using a looped strap as the holding means, the strap is typically comprised of interwoven strands of flexible material and preferably has a substantially narrow and flat configuration. The holding means may be secured to the article 10 at any location via any known securing methods such as those described above, with looping and tying being preferred. Preferably, the outer end of the strap 14 substantially extends beyond the exterior of the body 12. The strap 14 can be of any desired length but is preferably of a length suitable for forming a loop 16, which is large enough to permit a variety of hand sizes to fit therethrough. The material forming the strap can be either substantially inelastic or elastic. In a preferred embodiment, approximately 20 cm length of nylon filament is looped through a punched hole in the corner of article 10.

The following examples are intended to illustrate the article of the invention and its use. The examples should not be interpreted as limiting the scope of the invention.

EXAMPLES

Example 1

Preparation of the Filled Cells

A piece of 30 cm×30 cm water insoluble film available from S. C. Johnson & Son, Inc. under the tradename, "Saran Wrap" was folded in half. A model AIE300 Impulse heat sealer available from American International Electric, Inc. was used to seal one edge, utilizing a setting of 4 and a time length of 2 seconds. The film was moved to the right by 2 cm and sealed in a like manner to yield parallel seals which formed a tube or column. This heat sealing technique was used to form five columns, which were then filled with a liquid cleanser commercially available from Johnson & Johnson Consumer Companies, Inc. under the tradename, "Purpose Gentle Cleansing Wash."

After drawing the liquid cleanser into a disposable plastic pipet, the contained cleanser was then inserted into one of the columns in an amount sufficient to fill about ¾ of the column's volume. After each column was appropriately filled with cleanser, a drop of cosmetically acceptable dye was added to each column, with each column having a different color.

The individual cells were then formed by using the above heat sealing technique in the transverse direction in order to form rectangular cells. This sealing technique was repeated until a 5×5 matrix of cells were formed. The excess film was cut away with scissors.

Example 2

Preparation of the Article

A 10 cm×17.5 cm piece of Tredegar Vispor™ 6582 apertured film was folded over lengthwise and sealed along the periphery of the sides adjacent to the folded side in accordance with the procedure set forth in Example 1. The resulting film possessed an open end opposite to the fold side. Excess film was then cut away with scissors.

The 7.5 cm×7.5 cm bag so formed was then turned inside out to hide the seams. The cell layer prepared in accordance with Example 1 was then placed inside the bag. About twenty 1.25 cm×8 cm strips of Tredegar Vispor™ 6582 apertured film were inserted between the cell layer and the exterior apertured film layer. The open end was then heat sealed and the excess material was trimmed off with scissors. A hole was then punched in a corner of the resulting article and a 0.2 cm×25 cm strip of nylon filament was threaded therethrough and tied.

Example 3

Use of the Article

The article prepared in accordance with Example 2 above was used by 5 consumers who manually pressed on a section of the exterior layer of the article that corresponded to a cell in order to burst the cell and release the cleansing solution contained therein.

The article was then placed in contact with water for about 5 seconds, then squeezed to generate foam for washing. After the article was used on the consumer's body for about 10 minutes in a typical washing regiment, all remaining foam on the article was easily rinsed away therefrom. The article was then hung by the nylon filament to dry. The article dried within several hours.

When the article was used again in a similar washing regiment, the article produced a superior amount of foam, was easily rinseable, and quickly dried.

This Example showed that the article of the present invention provided a very useful and uncomplicated means of dispensing cleaning or treating solutions in an aesthetically pleasing manner. In addition, this Example showed that the article is quick-drying and capable of producing a superior amount of foam during use.

I claim:

1. A cleansing article comprising:

a first exterior layer;

a second exterior layer;

and a cell layer having a plurality of cells containing an active material, wherein at least one of the exterior layers is an apertured film and the cell layer is disposed between the first exterior layer and the second exterior layer, and wherein said apertured film is made from a polymer selected from the group consisting of polyester, polypropylene, polyethylene, ethylene vinyl acetate copolymer, metallocene polyethylene, blends thereof, and copolymers thereof; wherein at least one of the exterior layers contains an anti-bacterial agent, and wherein the article is reusable, easily cleaned and dried after use.

2. The article of claim 1 wherein the ethylene vinyl acetate copolymer has a vinyl acetate content of, based upon the total weight of the copolymer, from about 9 percent to about 28 percent.

3. The article of claim 1 wherein the aperatured film has an open area of no more than about 45%.

4. The article of claim 1, wherein the thickness of the cell film is from about 0.5 mil to about 3.0 mil.

5. The article of claim 1 wherein the at least one cell contains an active material that is prevented from escaping unless either pressure is applied or is dipped in a liquid which dissolves or disperses out the active material.

6. The article of claim 5 wherein the at least one cell contains an active material that is prevented from escaping unless pressure is applied.

7. The article of claim 1 wherein the active material is selected from the group consisting of moisturizers, bubble bath compositions, cleansers; toners; astringents; conditioners; sunscreens; shaving foams; tanning agents; anti-acne agents; anti-aging agents; anti-irritant agents; perfumes/fragrances; moisturizers and mixtures thereof.

8. The article of claim 7 wherein the active material is selected from cleansers, moisturizers, conditioners, and combinations thereof.

9. The article of claim 1 further comprising a core layer.

10. The article of claim 9 wherein the core layer is a material selected from the group consisting of non-wovens, wovens, sponges, open-celled foam selected from the group consisting of a natural source, a synthetic source, extruded plastic scrim, polymeric films, and mixtures thereof.

11. The article of claim 1 further comprising a hanging means.

12. The article of claim 11 wherein the hanging means is selected from the group consisting of straps, handles, knobs, hooks, a character figure, hooks and loops, magnets, plastics, rubbers, synthetic elastics, and combinations thereof.

13. The article of claim 1 further comprising a sensory device located in said article in locations that correspond to said at least one cell.

14. The article of claim 13 wherein the sensory device is a gas enclosed in a film.

15. The article of claim 1, wherein the first exterior layer has a first end and the second exterior layer has a second end, and the first exterior layer and the second exterior layer are removably attached along the first end and second end.

16. The article of claim 15 wherein a second cell layer may be inserted into the article when the active material in the first cell layer is expended.

17. The article of claim 1, wherein the at least one cell is comprised of a cell film selected from the group consisting of water insoluble films, water soluble films, oil insoluble films, and combinations thereof.

18. The article of claim 17 wherein the water insoluble film is selected from the group consisting of polyvinyl chloride, polyvinylidine chloride, polyethylene, polypropylene, vinyl chloride copolymers, ethylene vinyl alcohol, blends thereof and copolymers thereof.

19. The article of claim 17 wherein the water insoluble film has a moisture vapor permeability of from about 10 $g/m^2/24$ hr/day to about 50 $g/m^2/24$ hr/day.

* * * * *